US010233469B2

(12) United States Patent
Nouaille et al.

(10) Patent No.: US 10,233,469 B2
(45) Date of Patent: Mar. 19, 2019

(54) METHOD FOR EXTRACTING MOLECULES PRODUCED BY ANAEROBIC FERMENTATION FROM FERMENTABLE BIOMASS

(71) Applicant: Afyren, Saint Beauzire (FR)

(72) Inventors: Régis Nouaille, Cournon d'Auvergne (FR); Jérémy Pessiot, La Charite sur Loire (FR)

(73) Assignee: AFYREN, Saint Beauzire (FR)

( * ) Notice: Subject to any disclaimer, the term of this patent is extended or adjusted under 35 U.S.C. 154(b) by 0 days.

(21) Appl. No.: 15/327,522

(22) PCT Filed: Jul. 17, 2015

(86) PCT No.: PCT/FR2015/051964
§ 371 (c)(1),
(2) Date: Jan. 19, 2017

(87) PCT Pub. No.: WO2016/012698
PCT Pub. Date: Jan. 28, 2016

(65) Prior Publication Data
US 2017/0183696 A1     Jun. 29, 2017

(30) Foreign Application Priority Data

Jul. 25, 2014  (FR) ...................................... 14 57201

(51) Int. Cl.
| C12P 7/40 | (2006.01) |
| C12P 7/52 | (2006.01) |
| C12P 7/54 | (2006.01) |
| C12P 7/64 | (2006.01) |
| B01D 11/02 | (2006.01) |
| B01D 11/04 | (2006.01) |
| B01D 15/00 | (2006.01) |
| B01D 15/08 | (2006.01) |

(52) U.S. Cl.
CPC ............ *C12P 7/6409* (2013.01); *B01D 11/02* (2013.01); *B01D 11/04* (2013.01); *B01D 11/0492* (2013.01); *B01D 15/00* (2013.01); *B01D 15/08* (2013.01); *C12P 7/52* (2013.01); *C12P 7/40* (2013.01); *C12P 7/54* (2013.01)

(58) Field of Classification Search
None
See application file for complete search history.

(56) References Cited

U.S. PATENT DOCUMENTS

| 4,424,275 A | 1/1984 | Levy |
| 6,043,392 A | 3/2000 | Holtzapple |
| 2013/0164795 A1* | 6/2013 | Lowe ........................ C12P 7/16 |
| | | 435/134 |

FOREIGN PATENT DOCUMENTS

| EP | 0216221 A2 | 4/1987 |
| FR | 2588271 B1 | 4/1987 |
| WO | 2013022998 | 2/2013 |

OTHER PUBLICATIONS

National Center for Biotechnology Information. PubChem Compound Database; CID=6556, https://pubchem.ncbi.nlm.nih.gov/compound/6556 (created 2004) (Year: 2004).*
Yang, et al., "Extraction-Fermentation Hybrid (Extractive Fermentation)" Separation and Purification Technologies in Biorefineries, First Edition, Shri Ramaswamy, et al., eds. (2013) John Wiley & Sons, Ltd., pp. 409-437.
English translation of International Preliminary Report on Patentability in PCT/FR2015/051964, dated May 10, 2015, 8 pages.
English Translation of International Search Report in PCT/FR2015/051964, dated May 10, 2015, 3 pages.
English translation of the Written Opinion of the International Searching Authority in PCT/FR2015/051964, dated May 10, 2015, 7 pages.
Huang, et al., "A review of separation technologies in current and future biorefineries", Separation and Purification Technology 62 (2008), pp. 1-21.
Yang, et al., "Extraction-Fermentation Hybrid (Extractive Fermentation)", Separation and Purification Technologies in Biorefineries, Chapter 15 (Summary), John Wiley & Sons, published online Mar. 4, 2013, 3 pages.

* cited by examiner

*Primary Examiner* — Sean C. Barron

(57)  ABSTRACT

Process for extracting volatile fatty acids (VFA), organic molecules called precursors produced by microorganisms (M) in a fermentation reactor (2) by anaerobic fermentation (3) using fermentable biomass (1), said molecules being fermentative metabolites, comprising at least the following steps:
  a) selecting an extraction means (8) from extraction means that is, at least, insoluble in the fermentation medium and the processing conditions of which preserve the capacity of the microorganisms (M) present in the fermentation medium to produce the molecules,
  b) bringing the chosen extraction means (8) into contact (9) with the fermentation medium without interrupting the fermentation (3),
  c) recovering (12) the extracted molecules, at a pH lower than 4.5, by the extraction means (8) outside the fermentation reactor (2).

The invention also relates to an installation for implementing the method.

8 Claims, 1 Drawing Sheet

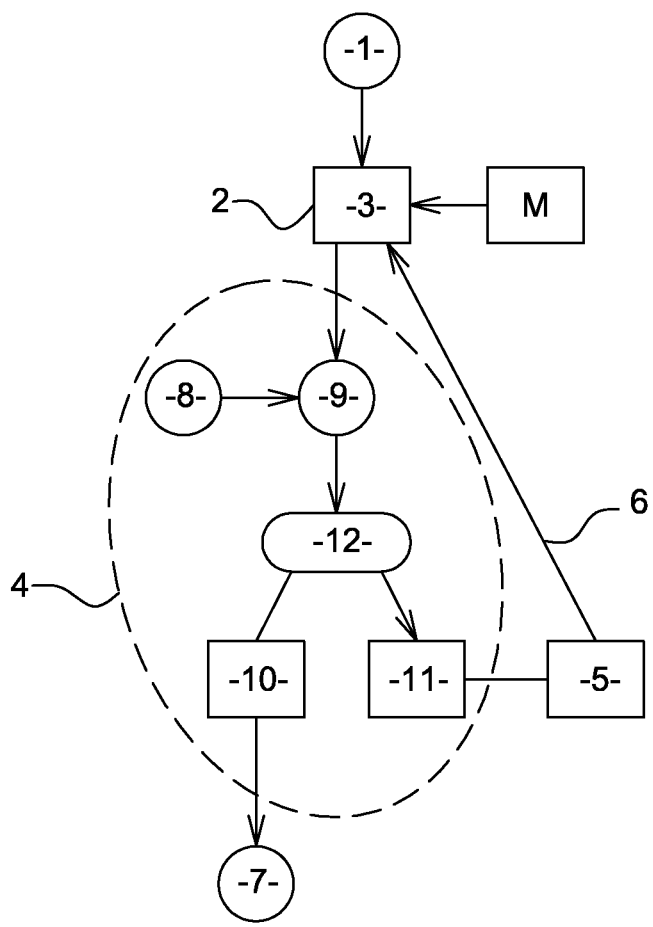

METHOD FOR EXTRACTING MOLECULES PRODUCED BY ANAEROBIC FERMENTATION FROM FERMENTABLE BIOMASS

CROSS REFERENCE TO RELATED APPLICATIONS

This is a National Phase entry of International Application No. PCT/FR2015/051964, filed Jul. 17, 2015, which claims priority to French Patent Application No. 1457201, filed Jul. 25, 2014, the disclosures of which are incorporated by reference in their entireties.

This invention relates to a process for extracting molecules produced by anaerobic fermentation from a fermentable biomass.

By fermentable biomass, herein is meant an organic substrate, which is advantageously non-food, obtained from waste, by-products and co-products formed of organic materials, that is to say the biomass results from human activities, whether they be of domestic, industrial, agricultural, forestry, aquaculture, agro-industrial, or livestock origin. By way of non-limiting example, mention may be made as an organic substrate, manures, the organic fraction of household refuse, slaughterhouse co-products, cellulosic or lignocellulosic residues originating from agro-industry such as those resulting from the transformation of sugar cane (bagasse), of sunflower seeds or soybeans.

Anaerobic fermentation denotes a fermentation carried out under anaerobic conditions by microorganisms, eukaryotes or prokaryotes, such as bacteria, fungi, algae or yeasts.

The term molecule herein refers to, preferentially but not exclusively, the so-called precursor fermentative metabolites. These precursors then make possible the production of molecules which have a greater energy and/or chemical interest, it being understood that these are organic molecules. Mention may be made with regard to molecules having an energy and/or chemical interest, for example, of molecules having a carbon chain comprised of acids, hydrocarbons, methane, esters, alcohols, amides or polymers.

Among the so-called precursor fermentative metabolites produced during fermentation, mention may be made of volatile fatty acids or VFAs which can be converted into, for example, ketones, alkanes, alcohols, alkenes, it being understood that such a fermentation also produces, among others, esters, gases, lactic acid, alcohols, hydrogen and carbon dioxide.

U.S. Pat. No. 6,043,392 discloses such a process for producing ketones by heat treatment of the volatile fatty acid salts obtained by anaerobic fermentation. Some of the volatile fatty acids are also converted into liquid hydrocarbons, aldehydes and alcohols. It turns out that this process is carried out in two distinct stages, namely the fermentation and then the treatment of the VFAs by extraction in the form of precipitated salts with a tertiary amine extractant. It is also known that the production of volatile fatty acids carried out by anaerobic fermentation induces an acidification of the medium which is detrimental to microorganisms. The acidification of the medium induces an inhibition of the microorganisms; therefore, it slows down or stops the fermentation, it is necessary to work in batches. For this purpose, the VFAs are extracted after a given fermentation time, by techniques known per se. The process therefore does not permit the rapid and continuous production of molecules called precursors, as the yield is not optimal. Anaerobic fermentation designed to produce butanol is known from U.S. Pat. No. 4,424,275. The extraction is carried out continuously with a solvent containing chlorine and fluorine. EP-A-216 221 discloses a liquid/liquid extraction associated with fermentation with a solvent that is non-toxic to microorganisms. Such processes consume strains of microorganisms and generate little or no recoverable waste.

The invention attempts to propose another extraction process making it possible to produce in a continuous, biocompatible, regular, and mastered manner, with a minimum of waste of very little value, diverse molecules, called precursors, obtained by anaerobic fermentation.

To this end, the subject-matter of the invention is a process for extracting volatile fatty acids (VFA), organic molecules called precursors produced by microorganisms in a fermentation reactor by anaerobic fermentation using fermentable biomass, said molecules being fermentative metabolites, characterized in that it comprises at least the following steps:
  a) selecting an extraction means from extraction means that are, at least, insoluble in the fermentation medium and the processing conditions of which preserve the capacity of the microorganisms present in the fermentation medium to produce the molecules,
  b) bringing the chosen extraction means into contact with the fermentation medium without interrupting the fermentation,
  c) recovering the extracted molecules, at a pH lower than 4.5, by the extraction means outside the fermentation reactor.

Such a process makes it possible to continuously extract molecules, in particular the so-called precursor metabolites, such as volatile fatty acids, while preserving the production capacity of the microorganisms present in the bioreactor. In fact, the extraction step makes it possible not only to continuously collect the molecules produced in the fermentation reactor, but also to preserve the microorganisms responsible for this production, the extraction being carried out under non-lethal conditions for all the microorganisms, that is to say under biocompatible extraction conditions. In this way, the problems associated with the accumulation of the precursors in the fermentation reactor are eliminated, for example from the acidification of the fermentation medium by the accumulation of the volatile fatty acids produced, which are harmful to the microorganisms. The activity of the microorganisms is maintained at a high level, close to the initial level, throughout the fermentation cycle.

According to advantageous but not obligatory aspects of the invention, such a method may comprise one or more of the following characteristics:
  The extraction means is a solvent having a boiling point lower than 70° C., as the extraction is of the liquid-liquid type.
  The extraction means is a solvent having a boiling point lower than the fermentation temperature.
  The extraction means is a solvent whose density is less than the density of the fermentation medium.
  The extraction means is a solid, the extraction being of the solid-liquid type.
  Placing the fermentation medium and the extraction medium in contact takes place in the reactor, the extraction means being isolated or not from the fermentation medium.
  Bringing the fermentation medium and the extraction means into contact takes place outside the reactor, the fermentation medium being sampled continuously.
  Bringing the fermentation medium and the extraction means into contact takes place outside the reactor, the fermentation medium being sampled sequentially.

After step c) at least one part of the liquid phase resulting from the extraction and reintroduced into the fermentation reactor and incorporated into the fermentation medium.

The invention also relates to an installation for implementing a method according to one of the preceding characteristics, characterized in that it comprises at least:

a fermentation reactor, an extraction component suitable for ensuring contact between the fermentation medium and the extraction means.

The invention will be better understood and other advantages thereof will be more clearly apparent upon reading the description of several embodiments of the invention given by way of non-limiting example and made with reference to the following drawings in which:

FIG. 1 is a simplified diagram representative of the process that is the subject-matter of the invention.

The various steps of the method are now described with reference to several embodiments, it being understood that the steps known per se are not detailed. In particular, reference will be made below to the diagram of FIG. 1 as illustrating an advantageous embodiment of the invention.

Firstly, the substrate 1 used is advantageously untreated, i.e., it has not undergone any physico-chemical or enzymatic pre-treatment. This substrate 1 consists predominantly of fermentable biomass. By way of non-limiting examples, mention may be made of agricultural or vegetable waste (straw, bagasse, corn stalks, grasses, wood, sheep clippings) paper waste (cardboard, paper), agri-food waste, slaughterhouse waste, the organic fraction of household waste, livestock manure (manure, slurry, droppings), algae, aquaculture waste, forestry waste or fermentable co-products from the cosmetic industry. Some substrates contain organic molecules, such as organic acids, which will not influence, or marginalize, the fermentation process. On the other hand, these molecules can be found in the fermentation medium and participate, for example, in the production of the final defined organic molecules.

The substrate 1 is introduced into a fermentation reactor 2, known per se and sized for the desired production, whether the latter is at laboratory scale for carrying out tests or at industrial scale in the case of production. In other words, the fermentation reactor 2 or bioreactor has a volume ranging from a few liters to several hundred cubic meters, as required.

Microorganisms are advantageously introduced initially into the fermentation reactor in an amount sufficient to start the fermentation. The microorganisms are advantageously inoculated in the form of a consortium, illustrated by the arrow M. The term consortium denotes a mixture or mixture of microorganisms, eukaryotes and prokaryotes, which may be bacteria, yeasts, fungi or algae. These microorganisms originate essentially from natural ecosystems, advantageously but not exclusively from anaerobic ecosystems such as, by way of non-limiting example, the anaerobic zone of aquatic environments such as the anoxic zone of certain lakes, soils, marshes, rumen of ruminants or intestines of termites. It should be borne in mind that the qualitative and quantitative distribution of the different types and species of microorganisms in the consortium M is not known precisely and above all may vary in significant proportions. It turns out that this qualitative and quantitative diversity imparts a surprising robustness and adaptability of the microorganisms which make it possible to ensure an optimal use of the substrates whatever the composition of the latter and under varying fermentation conditions.

Moreover, since the substrate 1 is used as it is, that is to say it is not sterilized or, more generally, it is not freed from the microorganisms which it contains before being introduced into the bioreactor 2, it appears that the microorganisms endemic to the substrate 1 are, de facto, incorporated into the consortium M or at least associated with the latter in the bioreactor 2.

The consortium M of microorganisms, associated with the microorganisms possibly present in the substrate 1, allows the fermentation 3 of the substrate 1, without adding products such as enzymes. Moreover, the fermentation 3 takes place under anaerobic conditions, more precisely when the redox potential is less than −300 mV, advantageously between −550 mV and −400 mV, and when the pH is lower than 8, preferably between 4 and 7. Fermentation 3 is advantageously limited to the production of the so-called precursor fermentative metabolites, namely volatile fatty acids or VFAs. A reaction is thus induced that is similar to the phenomenon of acidosis encountered in ruminants while having a methane production close to zero. Methane is generally one of the final fermentation metabolites obtained during anaerobic fermentation by microorganisms derived from natural ecosystems.

Fermentation 3 initially leads to the formation of volatile fatty acids having from one to eight carbons, mainly from two to four carbons, such as acetic acid, propionic acid and butyric acid. Long-chain volatile fatty acids, also greater than four carbons, such as valeric and caproic, heptanoic or octanoic acids are also obtained. By continuing the fermentation and/or increasing the quantity of microorganisms in the bioreactor 2, if necessary with selected microorganisms, it is possible to promote the production of long chain carbon chain VFAs, that is to say greater than four carbons.

In other words, the metabolites produced in quantity during fermentation 3 are essentially volatile fatty acids of two to six carbons. Subsequently, extraction will essentially concern the extraction of these metabolites, on the understanding that the process can be used for other molecules produced during other types of fermentation. Fermentation 3 may be carried out batch-wise, continuously, intermittently or fed-batch or preferably, continuously, in one or more fermentation reactors arranged in series.

Fermentation 3 is in all cases carried out to ensure the production of given molecules, i.e., VFA, in the liquid phase, it being understood that the invention relates to any type of organic molecules produced by fermentation or metabolites, since as much as possible, they are produced in the liquid phase. Thus, it is easy to conceive that the fermentation medium comprises a solid phase containing, at least initially, the solid fraction of the substrate 1 as well as the solid fraction of the consortium M of microorganisms. The liquid phase of the fermentation medium contains the molecules produced during the fermentation 3 as well as the liquid fraction of the substrate 1, at least at the start of fermentation.

The fermentation time varies, inter alia, as a function of the substrate 1, the microorganisms M present and the fermentation conditions. Typically, the fermentation period is between 1 and 7 days, preferably between 2 and 4 days. The concentration of metabolites obtained in the fermentation medium at the end of this period is variable, but, for example for volatile fatty acids, is generally on the order of 10 to 20 g/L, depending on the volatile fatty acids, on the understanding that under certain conditions it may be greater than 35 g/L, for example close to 50 g/L. At the end of the fermentation step 3, the pH of the fermentation medium is acidic, which is generally between 4 and 6, due to the presence of the volatile fatty acids in the fermentation medium.

When the production in metabolites, or predefined molecules, here in VFAs, by fermentation 3 of the substrate 1 reaches a defined quantity, generally in the steady-state phase of the fermentation, the extraction step 4 of the molecules is initiated. Preferably, but not obligatorily, this amount corresponds to a slowing down of the growth of the microorganisms, and thus in the vicinity of a threshold for inhibiting microorganisms.

The extraction means is chosen from the extraction means, liquid or solid, which are insoluble at least in the fermentation medium. When the extraction means is liquid, and therefore in the case of a solvent, the boiling point of the latter is advantageously less than 70° C. Preferably, the density of the solvent is lower than that of the fermentation medium.

More precisely, the extraction 4 is conducted with a solid or liquid extraction means 8, the processing conditions of which make it possible to preserve the activity and/or growth of the microorganisms M under the fermentation conditions prevailing in the bioreactor 2 and defined for carrying out the fermentation 3. The molecules, and thus the fermentative metabolites, are preferably extracted individually, or at least extracted by molecular families, from the liquid phase of the fermentation medium, which makes the best yields possible, among other things, and facilitates the production of specific compounds from these extracted molecules.

In all cases, the metabolites produced by the fermentation 3, here anaerobic, and which are, at least in part, extracted under conditions such that the extraction 4 does not destroy the microorganisms M, or at least in proportions where the continuation of the fermentation 3 is not appreciably modified by the microorganisms M present in the fermentation medium. In other words, the extraction means 8 is not lethal for all of the microorganisms. The extraction 4 therefore does not interfere or degrade the fermentation medium nor the fermenting capacities of the microorganisms M which it contains. The extraction 4 is therefore carried out under conditions such that it is biocompatible.

When molecules such as volatile fatty acids are extracted from the fermentation medium, de facto acidification of the fermentation medium is reduced by these acids. In this way, the fermentation, and thus the production of metabolites, continue under conditions similar to the initial conditions, with the acidity of the fermentation medium remaining low.

Advantageously, insofar as the extraction method chosen is not lethal for all of the microorganisms, it is found that the residual liquid phase 5, after extraction 4, may contain living microorganisms M, thus potentially active. As in this liquid phase 5 there are fewer volatile fatty acids than initially, the pH of the liquid phase 5 is less acidic. It is therefore possible to reinject it into the fermentation reactor 2, as illustrated by the arrow 6. Thus, not only is the phenomenon of acidosis reduced and/or the pH of the fermentation medium is lowered during fermentation 3, by extraction 4 of acidic compounds, but to some extent the medium is also re-seeded with microorganisms ensuring fermentation 3, without lowering the pH of the fermentation medium.

Such a solution makes it possible to optimize the yield of the fermentation 3 and to carry out a continuous fermentation, by lowering the fermentation times, while tending towards zero waste.

Extraction 4 is carried out continuously or sequentially, for example with an extraction every 12 hours. In other words, it is possible to continue the fermentation 3 while extracting the metabolites produced, either as they are produced or on a regular basis. Once extracted, the metabolites are purified and/or converted into other products 7, such as alkanes, alkenes, amides, amines, esters, polymers by chemical techniques known per se such as, distillation, synthesis, electrosynthesis, amidation or polymerization.

Liquid-liquid extraction with polar or non-polar organic solvents as the extraction means 8, is preferably, but not exclusively, the mode of extraction retained.

More precisely, when the extraction is of the liquid-liquid type, a mixture formed of the organic solvent 8 and the liquid phase originating from the fermentation medium is brought into contact 9, preferably with stirring, in order to facilitate the transfer of the aqueous phase to the organic phase.

After contact 9, the organic phase 10 and aqueous phase 11 are advantageously separated by decanting 12. At the end of the latter, the aqueous phase 11 is depleted of metabolites, in this case, volatile fatty acids, the organic phase 10 being enriched in metabolites, and thus in volatile fatty acids.

In one embodiment, the extraction is not carried out in a component separate from the fermentation reactor but directly in the latter. The solvent is, for example, introduced by a device of the bubbler type situated in the lower part of the reactor. In a variant, the extraction component is inserted into the volume of the reactor, a communication with the fermentation medium being provided.

It is then possible to reintroduce the aqueous phase 11, and thus possibly microorganisms M, into the bioreactor 2.

The so-called precursor metabolites are collected from the organic phase 10 by techniques known per se, such as distillation or evaporation. Advantageously, the organic solvent 8 is chosen to have a low boiling point and, in any case, in a range of non-lethal temperatures for the microorganisms, that is to say less than 70° C. In other words, the boiling point of the solvent is preferably below the fermentation temperature so that there are no traces of the solvent in the fermentation medium.

Moreover, the evaporation of a solvent with a low boiling point is inexpensive in energy and best preserves the molecules extracted, the temperatures reached to evaporate the solvent generating no thermal degradation of the molecules to be extracted.

In other words, the boiling point of the organic solvent is also advantageously lower than the boiling point of the extracted molecules.

Moreover, a density of the solvent lower than the density of the fermentation medium makes it possible to obtain, preferably, a supernatant in which the molecules are present. In the case where the extraction is carried out outside the bioreactor 2, any microorganisms present are then confined by gravity in the aqueous phase and in this way, are isolated from the supernatant and from the solvent 8. The inhibition is at least thus limited, if not the destruction of the microorganisms by the solvent.

Tests have been carried out by the applicant to extract volatile fatty acids according to various embodiments.

Test 1:

The volatile fatty acids produced during a fermentation which is carried out on a substrate comprising the fermentable fraction of household refuse at a concentration of 50 g/L in dry matter (MS) 0.50 ml of the fermentation medium, and thus the liquid phase, are recovered. The pH of this sample is 4.3. These 50 ml are then subjected, with moderate stirring 9, to an extraction with pentane as extraction means 8, using an equal volume of organic phase (i.e., 50 ml) and of aqueous phase.

After separating the organic 10 and aqueous 11 phases by decantation 12, 14.3 g/L of volatile fatty acids in the organic phase are recovered by evaporation of the solvent and 41.1 g/L of volatile fatty acids in the aqueous phase, or an extraction yield of 26%. 0.7 g of biosourced volatile fatty acids, that is to say from the fermentation 3 of the substrate 1, are recovered.

Test 2:

Test 1 was repeated but the sample taken in the fermentation medium was acidified with 10 M hydrochloric acid (HCl) to pH 2.25 instead of 4.3. After stirring 9, decantation 12 and evaporation of the solvent, in the organic phase, 18 g/L of VFA and 32.5 g/L of VFA in the aqueous phase are recovered in this manner. The extraction yield obtained in this case is 36%.

Test 3:

Test 2 was repeated using the same culture medium but by bringing the pH to 5.35 instead of 4.3 using a 10M NaOH solution. In this way, 6 g/L of VFA was recovered in the organic phase and 44.5 g/L of VFA in the aqueous phase. The extraction yield obtained in this case is 12%.

Test 4:

Test 1 was repeated with diethyl ether instead of pentane as the extraction means 8, and the influence of pH on the extraction yield was studied. The extraction yields obtained for a 1/1 di-ethyl ether extraction at different pH values which are as follows:

| pH | Extraction yield |
|---|---|
| 1.5 | 55% |
| 4.3 | 43% |
| 6 | 8% |

It therefore appeared that the yields obtained were different according to the pH conditions of the extraction, regardless of the liquid extraction means 8 retained, in this case an organic solvent. In particular, the Applicant found, surprisingly, that with a pH greater than 4.5, the yields drop. A pH lower than the initial pH of the fermentation medium, advantageously a pH of less than 3, will induce better extraction efficiency compared to an intermediate pH, it being understood that an intermediate pH will allow better extraction efficiency than with a pH higher than 6. These results were also unexpectedly observed for other types of solvents as illustrated by the results of Test number 5.

Test 5:

The influence of the nature of the solvent on the extraction yield with an acidified medium at a pH of less than 3 was studied. The results obtained were:

| Solvents | Extraction yield |
|---|---|
| Pentane | 36% |
| Cyclopentane | 35% |
| Hexane | 33% |
| Cyclohexane | 24% |
| Heptane | 30% |

It appears that the yields obtained are the highest using solvents such as pentane, cyclopentane or diethyl ether as seen in Test 4, it being understood that the yields are in all cases greater than 20%. It can be understood that the extraction means can be a mixture of at least two solvents, provided that the mixture is insoluble in the fermentation medium, at least. The solvents of greater interest insofar as their boiling point, are those with a lower boiling point, i.e., lower than 100° C., and more specifically between 30° C. and 70° C. This allows an extraction of the molecules directly into the reactor 2 without modifying the mesophilic or thermophilic mode. Moreover, although this type of solvent is quasi-insoluble in water, its low boiling point allows a good separation between the organic phase and the aqueous phase at the temperature encountered in the reactors during the fermentations.

The aqueous phase, which contains a smaller amount of volatile fatty acids than initially, and which has not been altered by the extraction 4, can be recycled, i.e., reintroduced into the fermentation reactor, to participate in the continuity of the fermentation 3.

A series of tests was conducted by modifying the solvent/solute ratio for liquid-liquid extraction. The extraction is carried out with a solvent/solute volume ratio of 2/1, instead of 1/1, on a fermentation medium similar to that of the first example. An extraction yield of 43% versus 36% in Example 1 was observed.

The test was repeated with a solvent/solute ratio of ½ in volume. The extraction yield was 27% compared with 36% in Example 1.

Therefore, we note that the extraction yield is improved by significantly increasing the proportion of solvent relative to the solute, without affecting the microorganisms.

Advantageously, the Applicant has found that it is possible to increase the liquid-liquid extraction yields by using one or more of the compounds frequently designated by the English term "extractant" in combination with the solvent or the mixture of solvents, that is to say a compound capable of reacting with a solute in a solution such as, inter alia, TBP (TriButylPhosphate). With a concentration of 10% of this extractant on a fermentation medium similar to Example 1, the extraction yield is 53% with pentane and 50% with hexane compared to 36% in Test 1 without extractant, with the pH and ratio conditions being similar to those of Test 1.

Tests have also been carried out with other extraction means, in particular with solid extraction elements, in the context of a solid-liquid extraction. These include resins, activated carbon or zeolites as such extraction means.

In all cases, solid extraction means is advantageously the most hydrophobic possible.

A test with the use of an anionic resin allowed an extraction yield of volatile fatty acids from a fermentation medium similar to that of the first Test of 22% in 15 minutes. Once the extraction step has been carried out, these solid means can be regenerated and used in other extraction steps.

Using activated carbon which had already been used and which was regenerated in order to extract the volatile fatty acids was tested on a fermentation medium similar to that of the first Test. Once the fermentation medium was reduced from a portion of the total volatile fatty acids, by extraction on the activated carbon, it was re-used for new anaerobic fermentations, with different consortia of microorganisms and on different substrates.

The results obtained from an extraction of the volatile fatty acids, regardless of the extraction type, show that the volatile fatty acid concentrations, for all fermentations, and therefore from different substrates and/or consortia of microorganisms, are all greater than the initial concentration of volatile fatty acids in the medium before fermentation over several generations of cultures. The fermentation activity was maintained using media which had undergone extraction steps. This shows that this process of liquid-liquid or solid-liquid extraction does not alter the characteristics of the fermentation medium and allows continuous production with at least partial recycling of the latter.

In situ extraction tests made it possible to show the biocompatibility of the extraction means, in other words the sequential or continuous recovery of molecules such as volatile fatty acids produced by microorganisms during a fermentation on a substrate during more than 2000 hours. This biocompatibility is characterized by the number of microorganisms per ml present in the bioreactor as determined by the flow cytometry analysis technique. These results are, for example, among the samples taken before and after in situ extraction, from $2.3.10^8$ to $8.0.10^7$ microorganisms/ml, in a series of measurements and from 2.9 to $2.3.10^8$ microorganisms/ml for another series of measurements. This shows that there is a decrease in the population of microorganisms present in the bioreactor, following the extraction of the molecules produced, that is to say in this case, volatile fatty acids, and therefore de facto, following sampling of the fermentation medium, but that this reduction does not lead to massive and total destruction of the microorganisms. The population of microorganisms is sufficient, quantitatively and qualitatively, so that the microorganisms are active and there is little or no loss of the fermentation activity in the consortium of microorganisms. In other words, fluctuations in the population of microorganisms, due to extraction, do not affect the overall activity of the microorganisms on a macroscopic scale, thus maintaining an optimal production of fermentative metabolites called precursors.

Extraction may thus be carried out, without irreversible stresses, directly in the fermentation reactor, whether it be a liquid-liquid or solid-liquid extraction.

It is therefore possible, in a preferred embodiment, to carry out a continuous fermentation with the in-situ extraction of the fermentation inhibiting metabolites, that is to say by extracting the volatile fatty acids responsible for acidosis of the medium, as they are produced or at least at regular intervals. In a variant not shown, these extraction operations can be carried out in a second compartment. In this case, a continuous or regular withdrawal of the fermentation medium takes place.

The implementation of such a method involves not only the presence in the installation of at least one fermentation reactor but also at least one extraction component, suitable for performing the extraction step. These components are known per se, their numbers and dimensions being adapted to the type of production, depending on whether the extraction is carried out inside or outside the reactor.

Such an installation advantageously comprises at least one component for storing the products resulting from the extraction. The means for management and control, such as temperature sensors, pH and/or redox probes, are provided. In addition, monitoring of microorganism activity is carried out by methods known per se, for example by analytical monitoring of the production of gaseous and liquid metabolites, counts using flow cytometry, molecular biology techniques such as molecular markers or biochips.

The invention claimed is:

1. A process for extracting volatile fatty acids (VFA) produced by microorganisms in a fermentation reactor by anaerobic fermentation using fermentable biomass, said volatile fatty acids (VFA) being fermentative metabolites, the process comprising the following steps:
   a) selecting liquid or solid extraction means that is insoluble in the fermentation medium and which preserves the capacity of the microorganisms present in the fermentation medium to produce said volatile fatty acids (VFA),
   b) bringing the extraction means into contact with the fermentation medium without interrupting the fermentation, thereby extracting the volatile fatty acids (VFA) from the fermentation medium,
   c) recovering the extracted volatile fatty acids (VFA) from the extraction means at a pH lower than 4.5, outside the fermentation reactor wherein the extraction means is a solvent having a boiling point lower than 70° C. and having a boiling point lower than the fermentation temperature.

2. The process according to claim 1, wherein the extraction means is a solvent whose density is less than a density of the fermentation medium.

3. The process according to claim 1, wherein the extraction means is a solid, and the extraction process is a solid-liquid type.

4. The process according to claim 1, wherein bringing the extraction means into contact with the fermentation medium takes place in the reactor.

5. The process according to claim 1, wherein bringing the extraction means into contact with the fermentation medium takes place outside the reactor, and the fermentation medium being is sampled continuously.

6. The process according to claim 1, wherein bringing the extraction means into contact with the fermentation medium takes place outside the reactor, and the fermentation medium is sampled sequentially.

7. The process according to claim 1, wherein, after step c), at least one part of a liquid phase resulting from the extraction process is reintroduced into the fermentation reactor and incorporated into the fermentation medium.

8. The method according to claim 1, wherein the extraction process is a liquid-liquid type.

* * * * *